United States Patent [19]

Williams

[11] Plant 4,729

[45] Jun. 2, 1981

[54] MINIATURE ROSE PLANT

[76] Inventor: Ernest D. Williams, 1510 Lebanon Ave., Dallas, Tex. 75208

[21] Appl. No.: 145,783

[22] Filed: May 1, 1980

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by the small well shaped buds and flowers, essentially a bi-color, the same being light to deeper shades of pink on upper petal surfaces and white to softer pink on reverse surface.

1 Drawing Figure

The present invention relates to a new and distinct variety of hardy, dwarf, bush type rose plant of the miniature class; the variety being primarily characterized — as to novelty — by small buds and flowers which in general color effect are similar to Toy Clown, a miniature variety (U.S. Plant Pat. No. 2,909).

The variety is further characterized by:

An abundance of bloom, with flowers usually borne singly on slender stem.

Fragrance: little or none.

A plant which is vigorous, of rounded somewhat upright shape with semi-glossy to glossy small foliage with pointed leaflets; the buds and flowers being similar in form and size to Kathy (miniature — U.S. Plant Pat. No. 3,246).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Over the Rainbow (miniature — U.S. Plant Pat. No. 3,472) as the seed parent and Over the Rainbow, as the pollen parent.

Subsequent to origination of the variety I successfully reproduced it, at my nursery located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Bit o'Magic.

Flowers borne: Usually singly, sometimes in clusters of 3 or more on slender wirey stems.

Quantity of bloom: Abundant both outside and in greenhouse.

Bud:

*Peduncle.*—Medium length; slender but sturdy; erect; medium green, sometimes tinted bronze (outdoors); Hairs — few or none.

*Before calyx breaks, size.*—Small. Form — medium length; pointed, with few to several foliaceous appendages on surface of bud; with foliaceous parts extending beyond the tip of the bud equal to one-half or less of its length. Color — medium green, occasionally tinted with bronze (outdoors).

*As calyx breaks, color.*—Whitish to light pink at base becoming deeper pink to red on upper portion. Opening: opens well in all weather.

Bloom:

*Size when fully open.*—Small, averaging about 25 mm (1"). Petalage — double — averaging about 45–55 petals, arranged regularly plus sometimes several small petaloids. Form — full with high center at first, becoming more open in the center, with petals reflexing loosely outward and downward. Open flowers show stamens.

Petals: Fairly thick; satiny on inside and on outside surface.

*Shape.*—Outside petals, broad lanceolate with pointed (acute) tip; inside — lanceolate with acute tip.

Color: Newly opened flower from a plant grown outdoors (August 1980), Dallas, Tex.

*Outside petals.*—Outside surface — white to near white becoming pinkish on tip ½ to ⅔ of petal. Inside surface — near Crimson 22 or lighter on tip portion of petal, quickly changing or blending into white or near-white at base.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — deep pink with near white reverse. Three days open — color similar to newly opened flowers but less brilliant. Behavior — opens well in all weather. Color lasts well. Spent petals drop off. Flower longevity (April 1980) — plant in pot 6–8 days or longer. Cut flowers at living room temperature 4–5 days or longer.

Reproductive organs:

*Stamens.*—Few, arranged regularly about pistils.

*Filaments.*—Varying length, fairly short, near white.

*Anthers.*—Well formed; yellow.

*Pollen.*—Little or none.

*Pistils.*—Average to small number.

*Styles.*—Fairly even; medium to short length; bunched.

*Ovaries.*—All enclosed in calyx.

*Hips.*—Usually none.

*Sepals.*—Permanent; spear shaped; remain against underside of flower.

*Seed.*—None.

Foliage:

*Leaves.*—Compound of five (sometimes three or seven) leaflets; small; leathery; semi-glossy to glossy.

*Leaflets.*—Shape: broad, nearly oval; apex acute; base rounded or rounded acute. Margin serrate. Color: medium to dark green; new growth — tinted reddish. Rachis: medium strength; grooved; underside sparsely thorny with few or no tiny prickles. Stipules: medium long; medium width; medium length; narrow points which turn out usually at about 45 degrees.

Growth:

*Habit.*—Dwarf; bushy; rounded; much branched.

*Growth.*—Free vigorous; internodes short.

*Canes.*—Medium; slender sturdy.

*Main stems.*—Color: medium green.

*Thorns.*—Fairly sparse; slender; hooked slightly downward; color, brown. Prickles — none. Hairs — none.

*Branches.*—Color: medium green. Thorns: few; medium length; slender; inclined downward. Medium to short oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, rounded, much branched habit, substantially as illustrated and described, characterized by bi-color buds and flowers, being essentially a deep pink to light red color on top surface of petal with the reverse surface being white or near white, the bud and flower resembling the Kathy miniature rose in general size and form; and further characterized by a plant of vigorous and compact growth habit, easy to propagate from cuttings, with an abundance of small size semi-glossy to glossy foliage and an abundance of flowers borne usually one to the stem.

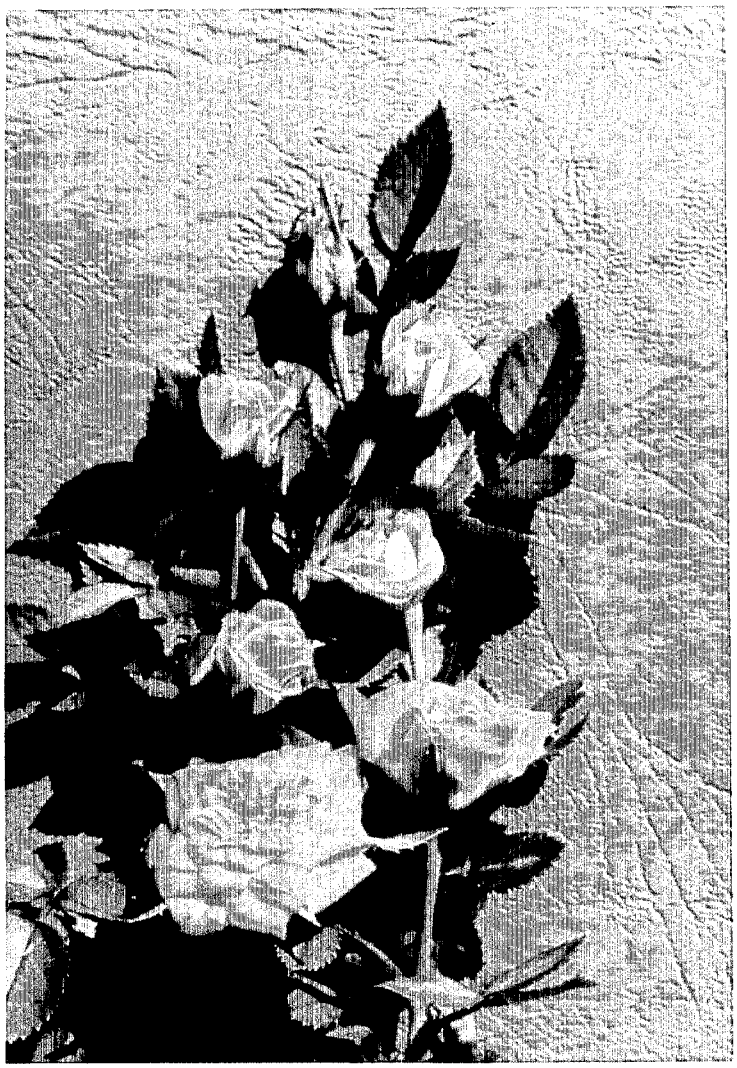

* * * * *